(12) United States Patent
Yayon et al.

(10) Patent No.: US 6,517,872 B1
(45) Date of Patent: Feb. 11, 2003

(54) FGFR3 AS A MARKER FOR MESENCHYMAL SKELETAL PROGENITOR CELLS

(75) Inventors: Avner Yayon, Moshav Sitria (IL); Zvi Nevo, Herzlia (IL)

(73) Assignees: Yeda Research and Development Co., Ltd., Rehovot (IL); Ramdt University Authority for Applied Research and Industrial Development Ltd., Tel Aviv (IL)

( * ) Notice: Subject to any disclaimer, the term of this patent is extended or adjusted under 35 U.S.C. 154(b) by 0 days.

(21) Appl. No.: 08/981,031

(22) PCT Filed: Jun. 12, 1996

(86) PCT No.: PCT/IL96/00010

§ 371 (c)(1), (2), (4) Date: Jun. 12, 1998

(87) PCT Pub. No.: WO96/41620

PCT Pub. Date: Dec. 27, 1996

Related U.S. Application Data

(60) Provisional application No. 60/000,137, filed on Jan. 12, 1995.

(51) Int. Cl.[7] .................. A61K 35/34; A61K 38/00; A01N 63/00; A01N 65/00
(52) U.S. Cl. ................. 424/548; 424/93.7; 530/300
(58) Field of Search ............... 424/93.7, 548; 530/300

(56) References Cited

U.S. PATENT DOCUMENTS 5,226,914 A 7/1993 Caplan et al.

OTHER PUBLICATIONS

Wakitani, et al. J. Bone Joint Surg Am. 76(4): 579–92, 1994.*
Thomson. et al. Bone 14, 779–786, 1993.*
Neuhaus, H. et al. Dev. Biol. 166(2): 531–42, 1994.*
Delezoide, AL et al. Mech. Dev. 77(1): 19–30, 1998.*
Peters, K et al. Devel Biol. 155: 423–30, 1993.*
Hecht, D. Growth Factors 12(3) :223–233, 1995.*
Baird, A. Fibroblast growth factors: activities and significance of non–neurtrophic growth factors. Current Opinion in Neurobiology, 4: 78–86, 1994.*
Mason, I.J. The ins and outs of fibroblast growth factors. Cell, 78: 547–552, Aug. 1994.*
Deng et al., "Fibroblast Growth Factor Receptor 3 Is a Negative Regulator of Bone Growth," Cell 84:911–921, 1996.
Erlebacher et al., "Toward a Molecular Understanding of Skeletal Development," Cell 80:371–378, 1995.
Hert, "Growth of the epiphyseal plate in circumference," Acta anat. 82:420–436, 1972.
Iwamoto et al., "Reduction in Basic Fibroblast Growth Factor Receptor is Coupled with Terminal Differentiation of Chondrocytes," J. Biol. Chem.. 266(1):461–467, 1991.
Langenskiöld et al., "Vital staining indicating cell migration towards the periphery in the growth plate," Acta. Orthop. Scand. 64(6):683–687, 1993.
Launay et al., "Comparative analysis of the tissue distribution of three fibroblast growth factor receptor mRNAs during amphibian morphogenesis," Differentiation 58:101–111, 1994.
Rousseau et al., "Mutations in the gene encoding fibroblast growth factor receptor–3 in achondroplasia," Nature 371:252–254, 1994.
Superti–Furga et al., "A glycine 375–to–cysteine substitution in the transmembrane domain of the fibroblast growth factor receptor–3 in a newborn with achondroplasia," Eur. J. Pediatr. 154:215–219, 1995.
Yamaguchi et al., "Fibroblast growth factors in mammalian development," Current Opinion in Genetics and Development 5:485–491, 1995.
Peters, K. et al., "Unique Expression Pattern of the FGF Receptor 3 Gene During Mouse Organogenesis," *Developmental Biology* 155(2): 423–430 (1993).
Keegan, K., "Identification and Characterization of an Additional Member of the Fibroblast Growth Factor Receptor Family, FGFR–3 (Leukemia Cell Line K562)," *Dissertation Abstracts International.* B. The Science and Engineering 52(9): 4594 (1992).
Hecht, D. et al., "Identification of Fibroblast Growth Factor 9 (FGF9) as a High Affinity, Heparin Dependent Ligand for FGF Receptors 3 and 2 but not for FGF Receptors 1 and 4," *Growth Factors* 12(3): 223–233 (1995).
McLeskey, S., et al, "MDA–MB–134 Breast Carcinoma Cells Overexpress Fibroblast Growth Factor (FGF) Receptors and Are Growth–Inhibited by FGF Ligands," *Cancer Research* 54(2): 523–530 (1994).

\* cited by examiner

*Primary Examiner*—Anthony C. Caputa
*Assistant Examiner*—Natalie Davis
(74) *Attorney, Agent, or Firm*—Fish & Richardson P.C.

(57) ABSTRACT

The present invention concerns fibroblast growth factor receptor 3 (FGFR3) as a novel marker for mesenchymal skeletal progenitor cells. By utilizing this novel marker it was possible both to identify and locate mesenchymal skeletal progenitor cells in a tissue, as well as to obtain a substantially pure culture of such cells. The pure culture of the mesenchymal skeletal progenitor cells may be used, optionally after various manipulations ex vivo, as an active ingredient in pharmaceutical compositions or implants for the purpose of bone and/or cartilage repair. FGFR3 may also be used as a marker for the identification and the localization of cartilage- and bone-derived tumors. Agents capable of binding to FGFR3 may also be used for targeting cytotoxic agents to cartilage- and bone-derived tumors.

10 Claims, 10 Drawing Sheets

US 6,517,872 B1

FGFR3 AS A MARKER FOR MESENCHYMAL SKELETAL PROGENITOR CELLS

This application claims benefit of provisional application 60/000,137 filed Jan 12, 1995.

FIELD OF THE INVENTION

The present invention concerns a method for identifying mesenchymal skeletal progenitor cells by identification of cells which feature on their surface fibroblast growth factor receptor 3 (FGFR3).

The present invention further concerns a method for obtaining mesenchymal skeletal progenitor cells by utilizing FGFR3-binding agents. The invention still further concerns a substantially pure culture of mesenchymal skeletal progenitor cells as well as pharmaceutical compositions and implants comprising said mesenchymal skeletal progenitor cells.

By another aspect the invention concerns a method for identification of cartilage-bony tumor and pharmaceutical compositions for the treatment of cartilage-bony tumor.

BACKGROUND OF THE INVENTION

Skeletal growth depends both on proper function of the tissue cellular elements—the chondrocytes, and their cell membrane receptors in the cartilaginous growth centers of the long bones, as well as on the normalcy and levels of circulating and local hormones and growth factors. Growth disorders are therefore classified into two distinct categories (a) failures in a circulating factor, and (b) failures in the target cartilaginous tissue.

The course of normal differentiation begins with mesenchymal stem cells which differentiate to skeletal progenitor cells which can either differentiate to precartilaginous stem cells, which eventually form the cartilage, or to preosteogenic stem cells which eventually form the bone.

In attempts to trace the mesenchymal stem cells supporting growth and their routes of migration in normals and in the family of growth disorders, there are difficulties, including the lack of proper markers for these specific mesenchymal stem cells. For example, spotty and incomplete information is available regarding the original location and the routes of migration of the growth plate stem cells, supporting the longitudinal and the transverse growth. A long lasting dispute of over a hundred years, which may be called "Ranvier versus La Cro2ix" is still perpetuating. In 1889 Ranvier stated "Cells forming the periosteal bone, originate from the cells of the growth plate", while in 1951 La Croix declared "Appositional growth occurs from cells of the peri-chondral periphery". Ranvier's theory gained support at the early seventies from Rigal, Hert, J. (Acta Anat (Bazel) 82:420–436 (1972)) and others, and in the nineties by Langenskiold et al. (Acta. Orthop. Scand., 64:683–687 (1993)), suggesting that cells from the germinal layer migrate to the borderline of the bone groove, serving as the source for both longitudinal and transverse bone growth.

A full understanding of the various types of cartilage cells and the factors that effect mesenchymal differentiation, however, has been hampered due to failure to locate the original location of the primary reservoir of these cells and thus the limitations of in vitro cell culture. One difficulty has been the lack of specific phenotypic markers to follow successive differentiation events. Type II collagen secretion is considered a major early marker of chondrocyte differentiation, while the synthesis of alkaline phosphatase is an early marker of osteoblast differentiation. Mature osteoblasts also produce osteopontin, osteonectin, and osteocalcin, three extracellular matrix proteins deposited together with type I collagen into mineralized bone matrix. Unfortunately, only a few differentiation markers have been identified, and several of these, such as alkaline phosphatase, osteopontin, and osteonectin, are not specific for osteogenic differentiation, while others, such as osteocalcin, are rarely expressed in vitro. In addition, mesenchymal cell lines and primary cultures of differentiating chondrocytes and osteoblasts display a variable phenotype and are often a mixture of cell types at different stages of differentiation (Eriebacher, A. et al, *Cell* 80:371–378, (1995); Yamaguchi, T. P. and Rossant, J., *Current Opinion in Genetics and Developmnent* 5:485–491 (1995)).

Thus it would have been highly desirable to develop a marker capable of locating precisely the site and source of stem cells supporting and contributing to both longitudinal and transverse growth and for bone repair both for better understanding of the mechanism of mesenchymal development in normal and pathological conditions, as well as for the purpose of obtaining a substantially pure culture of mesenchymal skeletal progenitor cells for therapeutical purposes.

SUMMARY OF THE INVENTION

The present invention is based on the surprising finding that fibroblast growth factor receptor 3 (FGFR3) serves as a marker for mesenchymal skeletal progenitor cells. The present invention is further based on the surprising finding that the anatomical location of mesenchymal skeletal progenitor cells is in the perichondrium in the La Croix groove.

The term "niesenchiymal skeletal progenitor cells" will be used in the following to denote the following types of cells: (a) mesenchymal stem cells which are able to differentiate to skeletal progenitor cells, (b) skeletal progenitor cells, (c) precartilaginous stem cells, and (d) preosteogenic stem cells or a combination of two or more of the above cell types. The mesenchymal skeletal progenitor cells all share the property of contribution to the growth of bone and/or cartilage, show enhanced proliferation properties as compared to other types of cartilage and bone derived cells and also a tendency to migrate in the presence of suitable chemotactic agents such as fibroblast growth factor 9.

These mesenchymal skeletal progenitor cells, in early stages of embryonal and neonatal life, support the growth of both articular and physis growth-plate cartilages. However, quite early in life, a few months post-birth, the connection of these stem cells to the articular zone is abolished leading to the poor self-wound healing of articular cartilage. Such mesenchymal skeletal progenitor cells continue to maintain the cell source for the longitudinal and latitudinal (transverse) growth of long bones, until the closure of the physis (at the age of 18–22 years), and continue to provide the stem cell reservoir of the periosteum, involved in the callous of bone fractures all through life. In adult life, especially at advanced ages, a technique for tracing undifferentiated cell source with a potential to establish proliferating chondrocytes has previously failed due to the scarcity of such a cell source and the inadequatability of markers for such undifferentiated cells.

By using the discovery on which the present invention is based, namely that FGFR3 is a marker for mesenchymal skeletal progenitor cells, it was possible to develop a method for identification of mesenchymal skeletal progenitor cells by identifying those cells which feature FGFR3 on their surface. Such a method may be important for tracing mesenchymal skeletal progenitor cells for example for better understanding of pathological conditions of growth arrest involving FGFR3 receptors for example those leading to genetic dwarfism-achondroplasia or persistent expression in multiple hereditary exostosis and reexpression in primary osteoarthritic osteophytes.

Thus the present invention provides a method for identifying mesenchymal skeletal progenitor cells comprising:
 (a) applying a fibroblast growth factor receptor 3 (FGFR3) binding agent to assayed cells or tissue under conditions allowing ligand-receptor binding;
 (b) determining which cells bound said FGFR3 binding agent, said cells being mesenchymal skeletal progenitor cells.
 The FGFR3 binding agent which may be an antibody or fibroblast growth factor 9 (FGF9) should be labeled and applied to the assayed tissue, for example to tissue of the joint. Those regions which are labeled serve as a source for mesenchymal skeletal progenitor cells.

Preferably, the source for the mesenchymal skeletal progenitor cells is the perichondrium at the region of La Croix, and the region which meets the synovial membrane and the periosteum.

The method of the present invention may be used to identify and locate mesenchymal skeletal progenitor cells in various tissues such as at the joints for various purposes, for example for obtaining a culture of mesenchymal skeletal progenitor cells, proliferating them in vitro and then reintroducing them to the body in order to encourage cartilage and bone growth. Alternatively, identifying these cells enables their removal from the tissue site in order to eliminate excess activity of such stem cells in various diseases and disorders characterized by over-activity of undifferentiated mesenchymal skeletal progenitor cells. Furthermore, by locating the regions of the FGFR3 carrying cells, it is possible to manipulate such cells in situ by administering to the exact location of these cells various modulating agents. Such agents may be agents capable of stabilizing the FGFR3 and thus maintaining for longer periods of time the undifferentiated proliferating state of these cells, an example being FGF9. Alternatively, the agent may cause premature differentiation of FGFR3 carrying cells, an example being an FGF9 antagonist.

By using the fact that FGFR3 is a marker of mesenchymal skeletal progenitor cells, it was possible for the first time to obtain a substantially pure culture of such cells from a non-embryonic source. According to the method of the present invention, by using the FGFR3 as a marker, it was found that the mesenchymal skeletal progenitor cells are located in the perichondrium ring (region of La Croix) present in the periphery of the growth plates. The poor self-wound healing of articular cartilage late in life may be explained on the basis of disconnection of these articular zones from the source of their potential stem cells at the perichondrial La Croix region which occurs at the cessation of growth.

Thus, the present invention enables not only localization of mesenchymal skeletal progenitor cells, but also obtaining for the first time a substantially pure culture of large amounts of such cells. The term "substantially pure culture" denotes a culture composed essentially of one or more of the four cell types covered by the term "mesenchymal skeletal progenitor cells" as defined above.

The present invention thus concerns a method for obtaining large amounts of mesenchymal skeletal progenitor cells from various sources, as will be explained hereinbelow. The mesenchymal skeletal progenitor cells may be identified, and separated from the other cells in the source, by utilizing either specific antibodies against FGFR3, or by using a specific ligand for this receptor such as the FGF9 ligand.

The method for obtaining a substantially pure culture of mesenchymal skeletal progenitor cells comprises:
 (c) applying an FGFR3-binding agent to a cell source containing mesenchymal skeletal progenitor cells; and
 (d) separating from said source only cells which are bound FGFR3, said cells providing a substantially pure culture of mesenchymal skeletal progenitor cells.

Separation may be carried out surgically, for example by picking up with a scalpel only those regions which are bound to an FGFR3 labeled binding agent, or may be carried out by utilizing various cell separation systems which are able to separate individual cells bearing a specific label (the FGFR3 binding agents) from an unlabeled population of cells in the source.

Suitable sources for obtaining such mesenchymal skeletal progenitor cells is an autogenic source available from arthroscopic or bone marrow biopsies. The biopsy source may be non-proliferating chondrocytes or dedifferentiated fibroblast-like cells. The cell source may also be obtained from regions of the perichondrium, synovial membrane or periosteum or the location in which these regions meet. Only by utilizing a specific marker it is possible to isolate mesenchymal skeletal progenitor cells from these sources due to the scarcity of these cells in the tissue. Alternatively the cell source may also be embryonic.

Mesenchymal skeletal progenitor cells obtained from these sources may be induced to proliferate ex vivo in the presence of suitable growth factors and heparin and then reintroduced into the body either in the form of pharmaceutical composition within a medium suitable for maintaining the viability of chondrocytes, or introduced to the desired site in the form of an implant, wherein the mesenchymal skeletal progenitor cells are present inside a growth-permissive gluey milieu. It is preferable that both the pharmaceutical composition and the implant contain also suitable fibroblast growth factor, preferably fibroblast growth factor 9, in order to stimulate the activity of the FGFR3 present on those mesenchymal skeletal progenitor cells.

The pharmaceutical compositions or the implant of the invention may be used for the purpose of repair and regeneration of defective articular cartilage, for treatment of achondroplastic patients, for treatment of patients suffering from other growth disturbances and for treatment of physical injuries with poor predicted rate of cartilage and bone growth. The pharmaceutical composition or the implant of the invention may be used as interventions for manipulating the rate of growth within growth plates in order to increase the growth rate and/or prevent premature differentiation; or may be used for direct injection into the nucleus pulposus of the fine vertebrae in order to enhance the healing of spine injuries. If desired, the autologous mesenchymal skeletal progenitor cells may be altered, ex vivo by molecular engineering to express desirable traits prior to introduction into the desired site. Examples of genetic manipulations are those directed to over-expression of wild type FGFR3 in order to replace a mutant defective receptor, or the expression of a dominant negative mutant FGFR3 in order to suppress the activity of a wild type receptor, for example, in the cases of various types of tumors and the like.

In practice, the method of the invention comprises embedding the mesenchymal skeletal progenitor cells in a viscous growth-permissive milieu, usually based on hyaluronic acid, forming a composite semi-solid implant. The implant is transferred to the target site of growth, for example the articular lesion site, either under open joint surgery or by an arthroscopic device, filling the lumen of the injury to the articular surface. A thin permeable film is formed by a spraying device, closing the defect and ensuring the anchorage and maintenance of the implant in its authentic place.

By another aspect, the present invention is based on the finding that FGFR3 is also present on cartilagineous-bony tumors, for example, benign tumors (e.g. exostosis and osteophytes) and thus may serve both as an indicator of the presence of such a tumor as well as a marker for the precise localization of such tumors. Therefore, the present invention further comprises a method for detection of cartilaginous-bony tumors in a tissue or a sample comprising:

(i) contacting the assayed tissue or sample with an FGFR3 binding agent;

(ii) detecting the presence of cells which bound FGFR3 binding agent a positive detection indicating the presence of a cartilaginous-bony tumor in the assayed tissue or sample.

The detection may be carried out by using suitable labeled antibodies against FGFR3, or by use of specific labeled ligands for FGFR3, such as FGF9. By applying said labeled FGFR3 binding agent to a tissue in vivo it is possible not only to determine whether a tumor is present in the tissue, but also to precisely localize the tumor which may help in surgical removal thereof.

The fact that the FGFR3 is present on cartilaginous-bony tumor cells, may also serve to target cytotoxic agents specifically to the site of the tumor, by attaching to a specific ligand to FGFR3 such as FGF9, or a specific antibody against FGF9, a suitable cytotoxic moiety. Thus the present invention is further directed to pharmaceutical compositions for the treatment of cartilaginous-bony tumors comprising an FGF3 binding agent attached to a cytotoxic moiety, as well as to a method for the treatment of such tumors by administering to a subject a therapeutically effective amount of FGFR3 attached to a cytotoxic moiety.

Cytotoxic agents are well known in the art and this term, within the context of the present invention, refers to any agent capable of destroying cartilage and bone-derived tumor cells. Examples of such agents are, for example methotrexate, doxombicin, cyclophosphamides. etc.

Treatment of cancer may also be carried out by inducing differentiation of FGFR3 carrying cells. This may be carried out for example by introduction of FGFR3 differentiation inducing agents to regions labeled by a FGFR3-binding agent. Examples of differentiation inducing agents are FGF9 antagonists or antibodies against FGF9.

The treatment may also be carried out by introducing to the tumor a dominant negative detective FGFR3 (for example, by genetic engineering) which attenuates the activity of the wild type FGFR3.

In the following the invention will be illustrated with reference to some non-limiting drawings and examples.

DETAILED DESCRIPTION OF THE DRAWINGS

FIG. 1 Histological staining of guinea pig epiphyseal sections by antibodies against FGFR3. The photomicrographs in FIGS. 1A–F represent sections through the epiphyses of young adult guinea pigs.

Figure 1A:
FIG. 1A is a photomicrograph of a sagittal section stained with the histological dye Masson's trichrome (magnification×6) which is a stain for connective tissue elements such as collagen and proteoglycans.
Figure 1B:
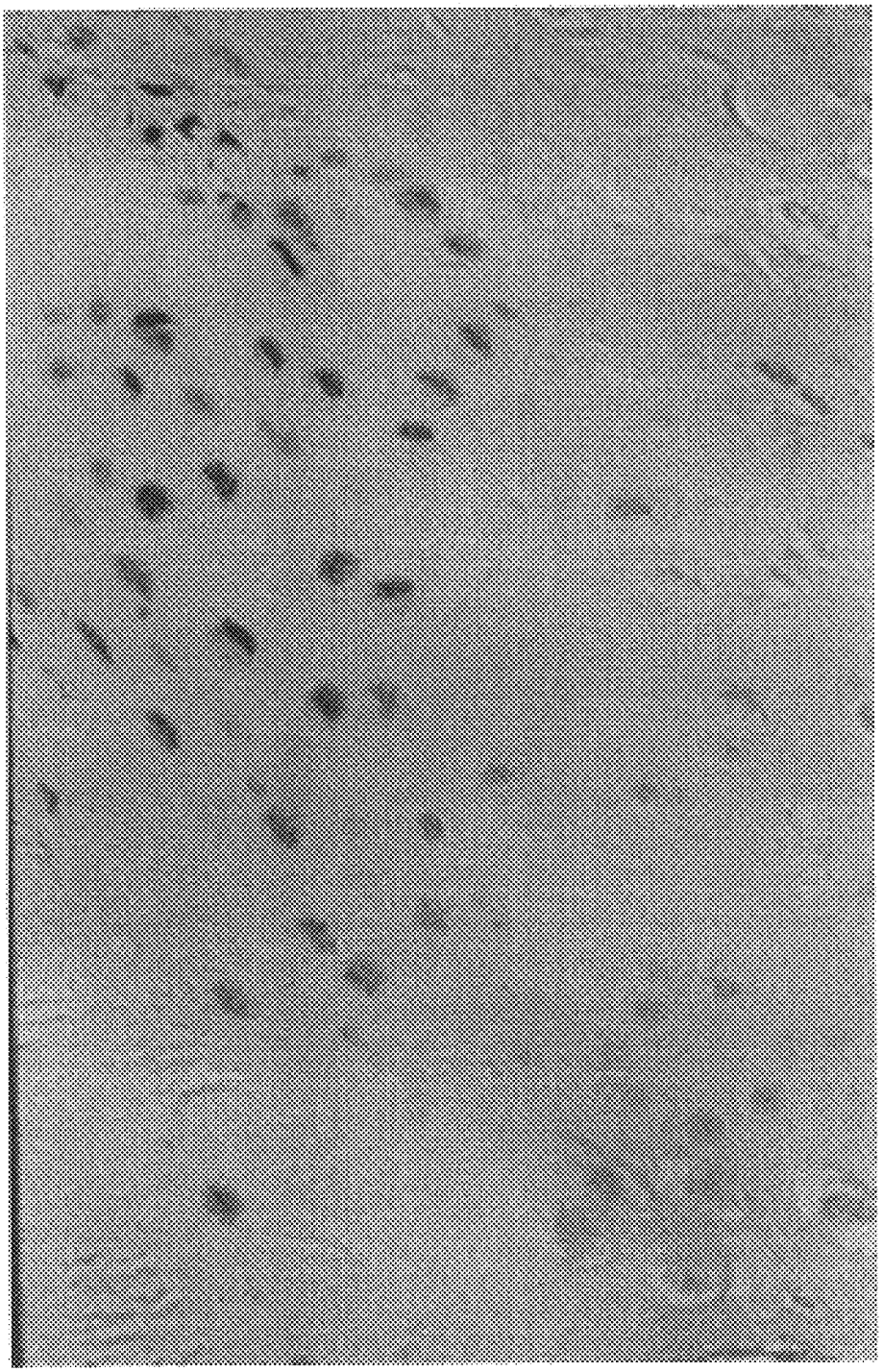
FIG. 1B is a photomicrograph of a sagittal section stained by immunohistochemical staining with antibodies against FGFR3 (×400).
Figure 1C:
FIG. 1C is a photomicrograph of an axial section stained by immunohistochemical staining with the antibody against FGFR3 (×400)
Figure 1D:
FIG. 1D is a photomicrograph of an axial section stained by masson's trichrome (×25).
Figure 1E:
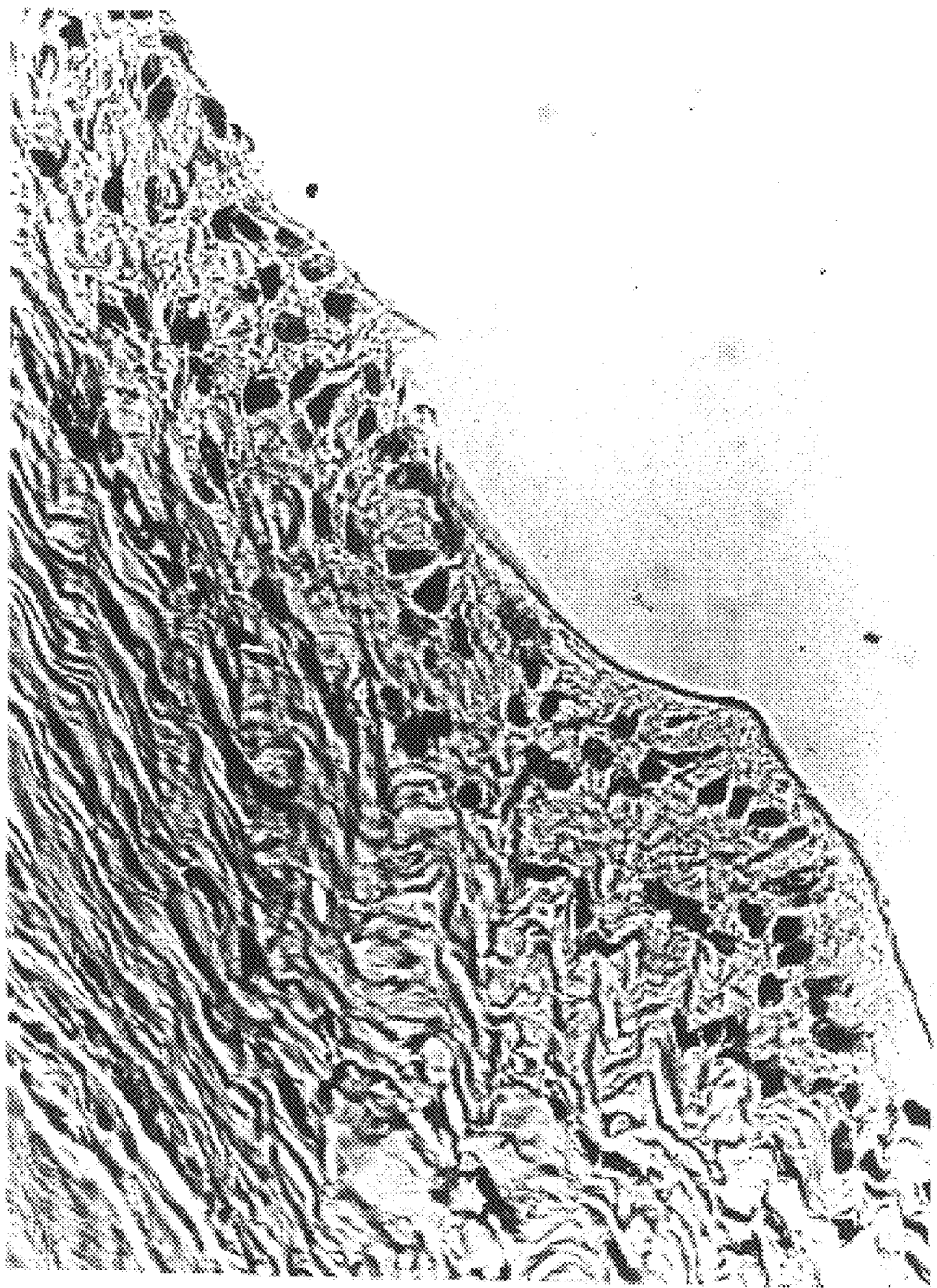
FIG. 1E is a photomicrograph of an axial section stained by immunohistochemical staining with the antibody against FGFR3 (×400).
Figure 2A:
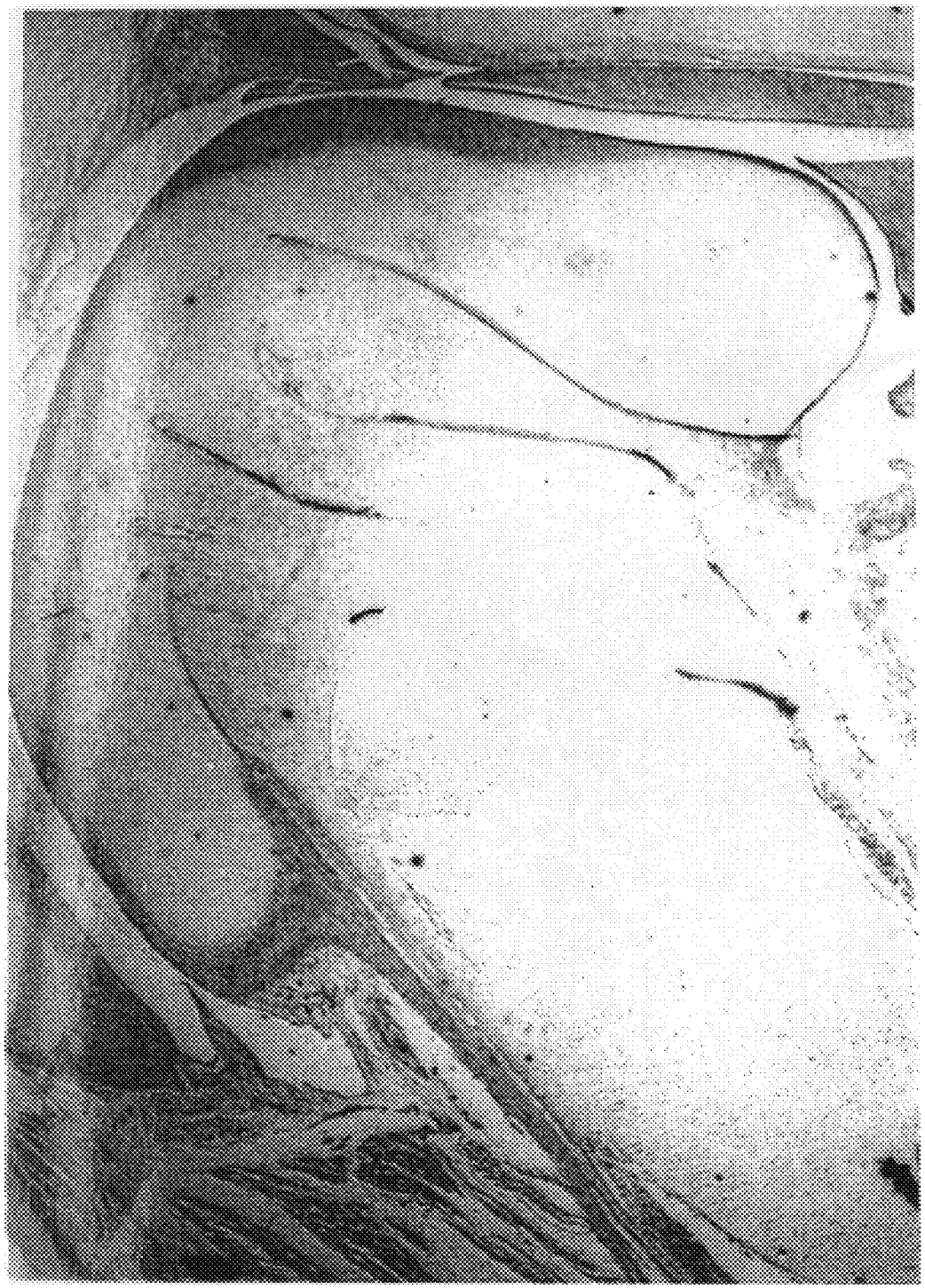
FIG. 2 is a series of photomicrographs (FIGS. 2A-F) representing sagittal sections through the epiphyses of long bones of 17 day old chick embryos.
Figure 2B:
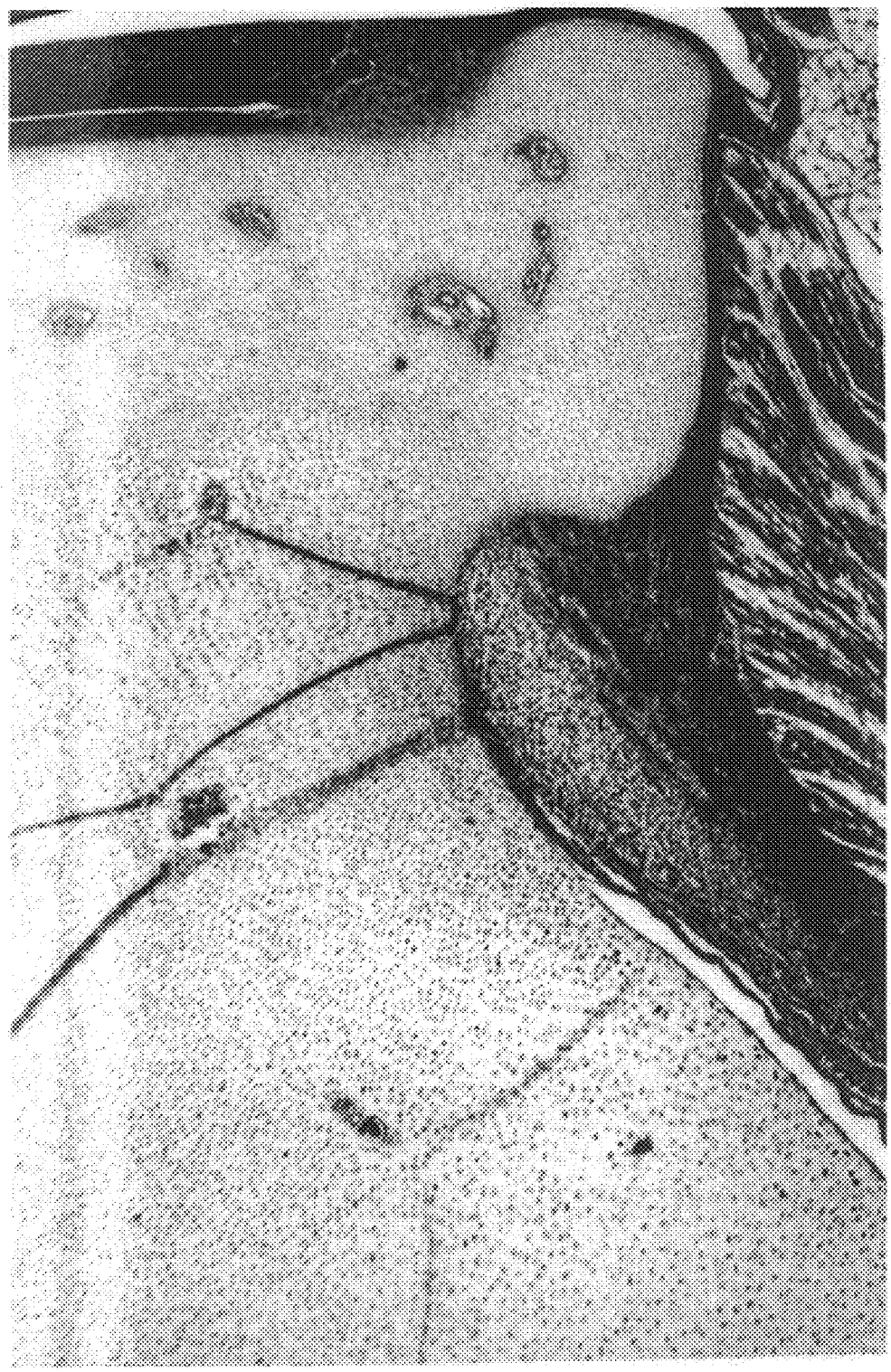
Figure 2C:
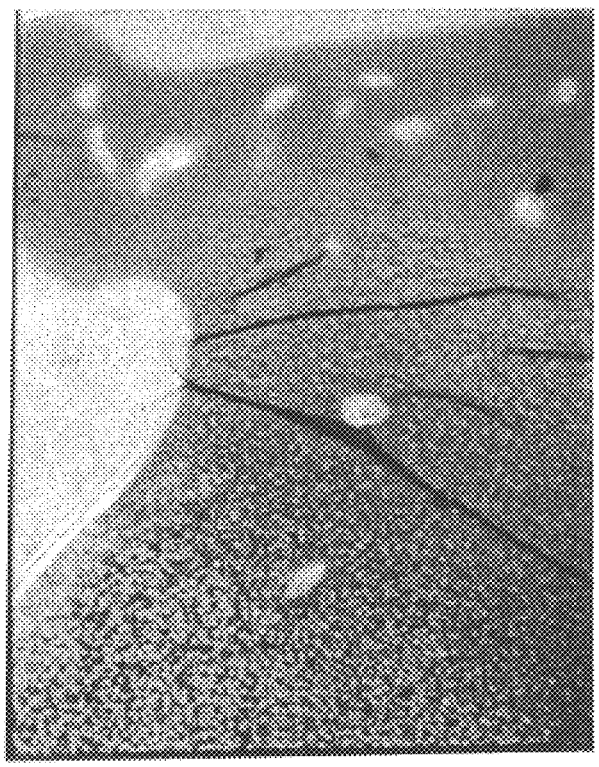

The sections shown in the photomicrographs in FIGS. 2A, E and F are stained by immunohistochemical staining with antibodies against FGFR3 and the section shown in FIG. 2C is stained by Alcian blue pH 2.5 specific for protoglycans (note lack of staining in certain areas).

Figure 2D:
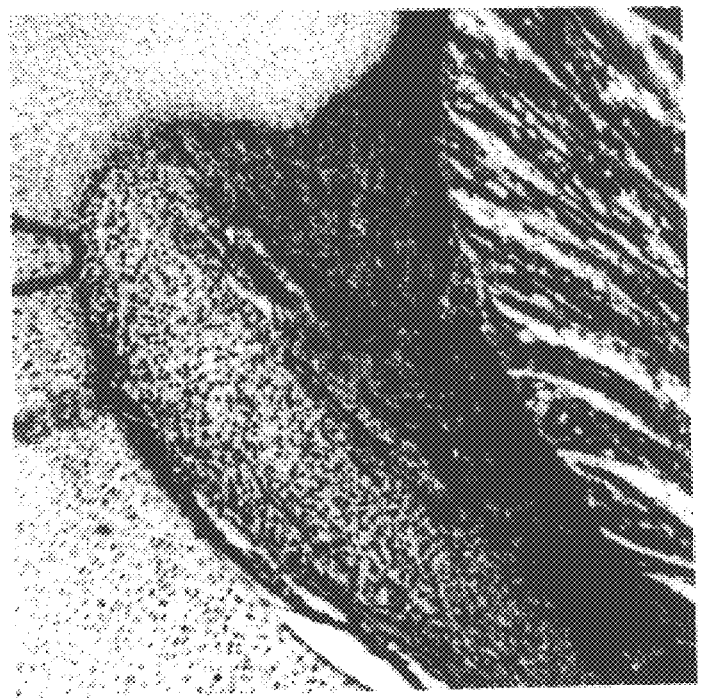
Figure 2E:
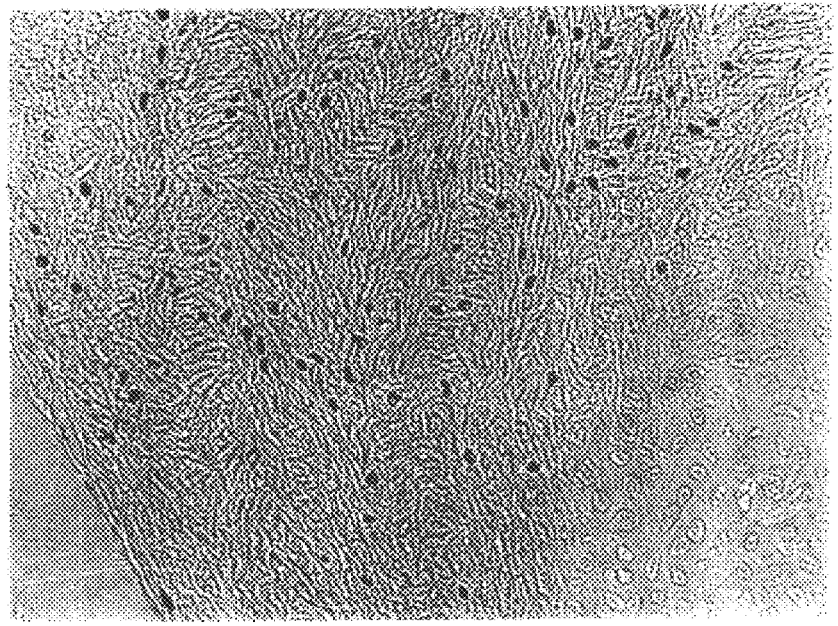
Figure 2F:

The photomicrographs were taken at the following magnifications: FIG. 2A (×25); FIG. 2B (×40); FIG. 2D (×100); FIG. 2E (×400); and FIG. 2F (×100).

The sections shown in FIGS. 2B and D were stained by Masson's trichrome.

Figure 3:
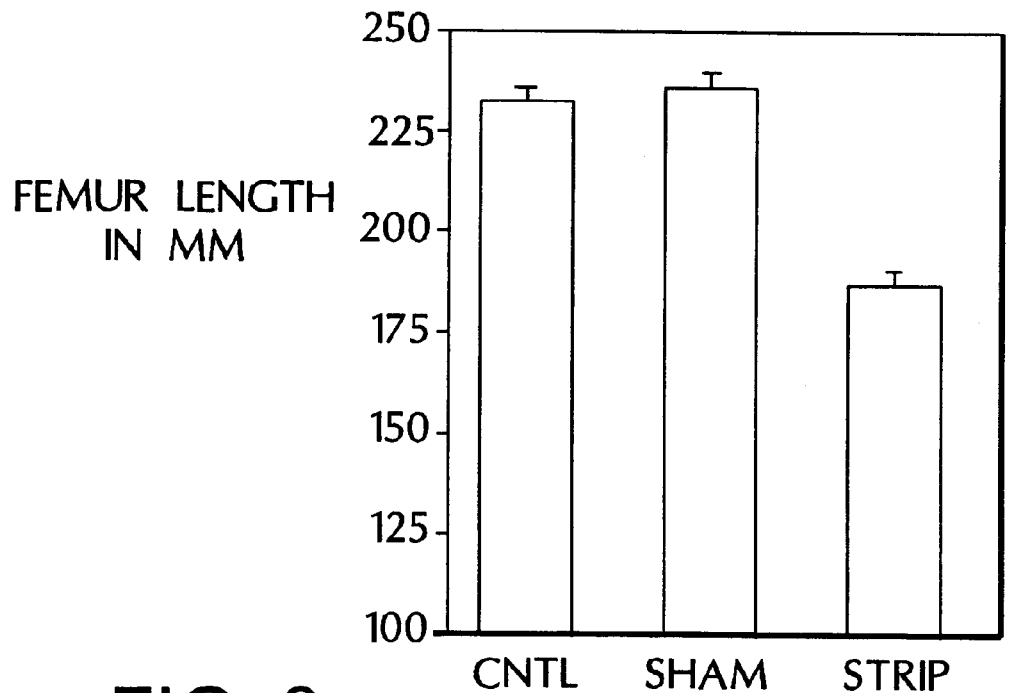

FIG. 3 shows the femur growth in adolescent rats in which the perichondrial ring surrounding the physis was removed (STRIP); in rats which underwent exposure of perichondrium without its removal (SHAM); and in rats which did not undergo any operation (CNTL).

Figure 4:
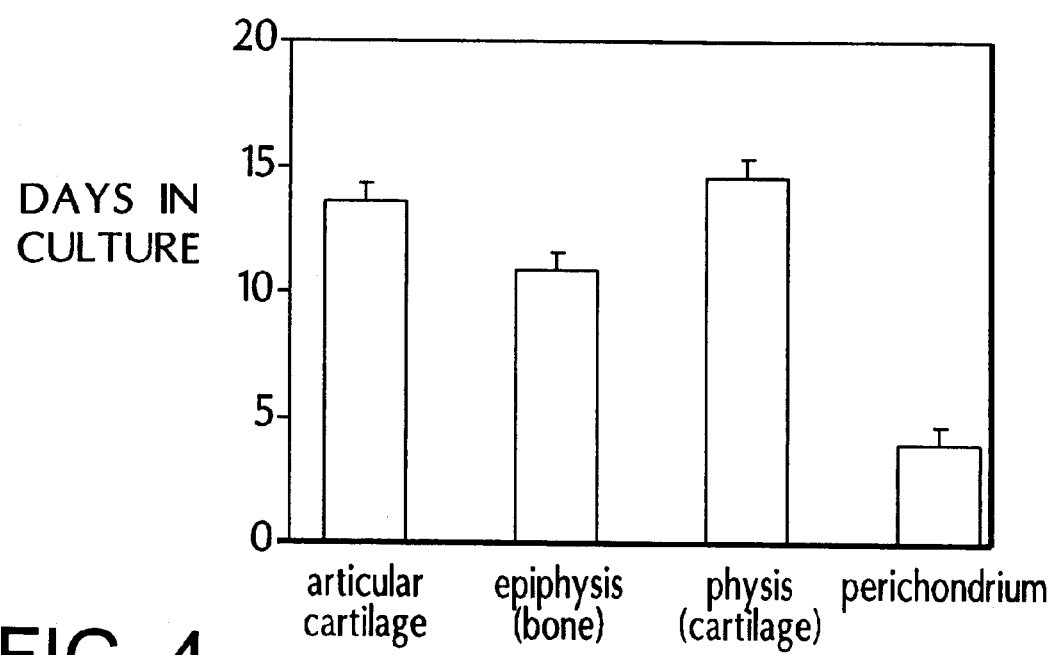

FIG. 4 shows the number of days until colony formation of cells, grown in vitro, obtained from articular cartilage, epiphysis, physis and perichondrium.

DETAILED DESCRIPTION OF THE INVENTION

Materials and Methods (a) Primary Chondrocyte Culture:

Epiphysis of long bones (femur and tibia) were obtained from 11 days old chicken embryos. After dissection, tissue segments were treated with trypsin in Tyrod's solution and mechanically disrupted until free cell suspension was obtained. Cells were then plated in high concentration ($5 \times 10^6$).

(b) PCR Screening of Primary Chondrocyte Cultures:

When confluence was reached, cells were collected and lysed by RNA purification kit (tri-reagent) (Molecular Research Center, Cincinnati, Ohio). RNA from cells was phenol extracted, isopropanol precipitated, resuspended in water, and assayed by measuring its optic density. After obtaining clean RNA (O.D. 260/280nm.>1.5), cDNA using reverse transcriptase reaction was made and screened for fibroblast growth factors (FGFs). The polymerase chain reaction (PCR) technique was used, employing oligonucleotide pairs for both FGFR3 and FGF9. Denaturation was at 94° C., annealing at 52–65° C., and elongation at 72° C., repeated for 35 cycles.

(c) Radiolabeling of FGF9:

Recombinant mouse FGF9 was prepared as previously described (Hecht, D. et al, Growth factors 12, 223–233 (1995)) labeled with $Na^{125}I$ (0.5mCi) using the Chloramine-T method and separated from free iodine on a heparinsepharose column. The range of specific activity was 0.5–2×105 cpm/ng.

(d) Immunohistochemistry:

Decalcified bones were embedded in liquid paraffin after fixation by formalin and picric acid. Paraffin blocks were cut and prepared for immunohistochemistry using a standard protocol. Staining of slides was done with ascending titer of anti-FGFR3 antibody.

(e) In Situ Hybridization:

T7 (antisense probe) and T3 (sense probe) were made from recombinant FGF9 and FGFR3 containing plasmid (Bluescript-Stratagen), using S-35 labeled uridine residues. Mouse embryos aged 10.5 to 18.5 days post-conception were fixed in paraformaldehyde, dehydrated in ascending concentrations of ethanol, and embedded in liquid paraffin. Sections were cut and prepared and hybridized with a proper RNA probe by standard methods.

EXAMPLE 1

Histochemical Staining by Antibodies Against FGFR3

As can be seen in FIG. 1, regions which were stained with antibodies against FGFR3 did not correspond to regions stained by Masson's trichrome which is an accepted cartilage stain. These findings indicate that FGFR3 bearing cells are not located in the cartilage itself but rather in the perichondrium in the region known as La Croix groove.

EXAMPLE 2

Stripping of the Ring of La Croix in Adolescent Rats 10 rats were included in each of three groups. Group 1 served as a control group (CNTL). Rats were anesthetized but no operation was performed. Group 2 (SHAM) served as a sham operation group and underwent anesthesia and dissection of soft tissues exposing the perichondrium. Group 3 (STRIP) underwent stripping of the perichondrial ring surrounding the physis under loop magnification which allowed dissection of the soft tissues only without any damage to the physis itself. 4 weeks later average femur length was measured in rats and the results are shown in FIG. 3. The contra-lateral limb was similar in length in operation to the control limbs (data not shown). The sham operated limbs demonstrated a tendency for increase in limb length which did not reach statistical significance. The stripped limbs demonstrated a growth arrest of the limb. These results indicated that removal of regions which were stained by FGFR3-antibodies causes arrest in limb length indicating the involvement of such regions in normal growth.

EXAMPLE 3

In Vitro Growth of Cells Obtained from the Ring of La Croix

Perichondrial tissue from the La Croix region removed from the above rats was placed in a culture dish in a suitable growth medium and the period until colony formation was determined. In comparison, tissue obtained from various locations of the distal femur (articular cartilage, epiphysis (bone), physis (cartilage)) was cultured under the same conditions and the period until colony formation was also determined.

As can be seen in FIG. 4, tissue removed from the perichondrium demonstrated an ability to rapidly form cell colonies after about 3 days in culture, while tissue removed from other regions formed cultures only after more than ten days from implantation. These results again indicate that cells obtained from the region stained with FGFR3-antibodies grow more rapidly than cells obtained from other regions of the bone which do not feature FGFR3.

EXAMPLE 4

Presence of FGFR3 in Exostosis

Antibodies against FGFR3 were applied to tissue obtained from exostosis benign tumor. The antibodies stained cells in the fibrotic tissue and essentially did not stain cells of the cartilage (data not shown). These findings indicate that FGFR3 is present in cartilaginous-bony derived benign tumor (exostosis) so that FGFR3 binding agents (such as antibodies) may be used to identify such tumors as well as to target cytotoxic agents thereto. This finding also leads to the treatment of such tumors by agents which cause disappearance of FGFR3 (for example antagonist of FGF9) and thus lead to differentiation.

What is claimed is:

1. A culture comprising skeletal progenitor cells, wherein the skeletal progenitor cells are the progeny of cells that (a) are obtained from a skeletal tissue and (b) are enriched in vitro for cells that express fibroblast growth factor receptor 3 (FGFR3) on their surfaces.

2. Skeletal progenitor cells obtained by a method comprising:

(a) applying an FGFR3-binding agent to a cell source containing skeletal progenitor cells, wherein the cell source is obtained from skeletal tissue; and (b) separating from said cell source cells to which the FGFR3 binding agent is bound, said cells to which the FGFR3 binding agent is bound providing a plurality of skeletal progenitor cells enriched in vitro for cells that express FGFR3 on their surfaces.

3. A pharmaceutical composition for the repair of bone and cartilage, the composition comprising: (a) a medium suitable for Maintaining the viability of chondrocytes; and (b) the culture of skeletal progenitor cells of claim.

4. A pharmaceutical composition according to claim 3, further comprising a member of the fibroblast growth factor (FGF) family that binds to FGFR3.

5. A pharmaceutical composition according to claim 4, comprising fibroblast growth factor 9 (FGF9).

6. A culture of skeletal progenitor cells derived from the perichondrium.

7. A culture according to claim 2, wherein the skeletal progenitor cells are precartilaginous stem cells.

8. A pharmaceutical composition for the repair of bone and cartilage, the composition comprising: (a) a medium suitable for maintaining the viability of chondrocytes; and (b) the skeletal progenitor cells of claim 2.

9. A pharmaceutical composition for the repair of bone and cartilage, the composition comprising: (a) a medium suitable for maintaining the viability of chondrocytes; and (b) the culture of skeletal progenitor cells of claim 6.

10. A pharmaceutical composition for the repair of bone and cartilage, the composition comprising: (a) a medium suitable for maintaining the viability of chondrocytes; and (b) the culture of precartilaginous stem cells of claim 7.

* * * * *